US011141503B2

(12) United States Patent
Lamboux et al.

(10) Patent No.: US 11,141,503 B2
(45) Date of Patent: *Oct. 12, 2021

(54) DEVICE FOR DIFFUSING A FRAGRANCE, SUCH AS A SCENT

(71) Applicant: TECHNIPLAST, Louviers (FR)

(72) Inventors: Jean-Philippe Lamboux, Saint Didier des Bois (FR); Frederic Simian, Saint Etienne du Vauvray (FR)

(73) Assignee: TECHNIPLAST, Louviers (FR)

( * ) Notice: Subject to any disclaimer, the term of this patent is extended or adjusted under 35 U.S.C. 154(b) by 126 days.

This patent is subject to a terminal disclaimer.

(21) Appl. No.: 16/266,856

(22) Filed: Feb. 4, 2019

(65) Prior Publication Data
US 2019/0240368 A1 Aug. 8, 2019

Related U.S. Application Data

(62) Division of application No. 14/907,676, filed on Jan. 26, 2016, now abandoned.

(51) Int. Cl.
*A61L 9/12* (2006.01)

(52) U.S. Cl.
CPC .................................. *A61L 9/127* (2013.01)

(58) Field of Classification Search
CPC .............................. A61L 9/127; A61L 2209/13
USPC ..................................................... 239/34–60
See application file for complete search history.

(56) References Cited

U.S. PATENT DOCUMENTS

| | | | |
|---|---|---|---|
| 2,766,069 A | 10/1956 | Tennyson | |
| 5,263,274 A * | 11/1993 | Speed ................. | A01M 31/008 222/108 |
| 2006/0231641 A1 | 10/2006 | Uchiyama et al. | |
| 2006/0233538 A1 * | 10/2006 | Tollens ................... | A61L 9/037 392/390 |
| 2011/0139829 A1 | 6/2011 | Lamboux | |
| 2012/0234432 A1 | 9/2012 | Lamboux | |

FOREIGN PATENT DOCUMENTS

| | | |
|---|---|---|
| EP | 2500277 | 9/2012 |
| WO | 2011128604 | 10/2011 |

OTHER PUBLICATIONS

Search Report dated Nov. 27, 2014.
Chinese Office Action dated Jun. 16, 2017.

* cited by examiner

*Primary Examiner* — Qingzhang Zhou
(74) *Attorney, Agent, or Firm* — Ipsilon USA, LLP

(57) ABSTRACT

A Fragrance diffusion system is provided having a diffusion device which has two opposing walls spaced apart from one another, at least one wick, and at least one air intake. An upper first bottle has a first neck the opening of which is positioned facing one of the two opposing walls referred to as the upper wall, a lower second bottle having a second neck the opening of which is positioned facing the other wall referred to as the lower wall. The upper first bottle has the fragrance which, by impregnating the wick, on the one hand causes the fragrance to diffuse into the cavity and to outside of the device via said at least one opening, and on the other hand causes dripping drop by drop into the lower second bottle. The lower second bottle having a capacity which is dimensioned so that the level of the liquid transferred into said lower second bottle is situated below a lower end of the wick.

14 Claims, 3 Drawing Sheets

DEVICE FOR DIFFUSING A FRAGRANCE, SUCH AS A SCENT

RELATED APPLICATION

This application is a divisional application from U.S. patent application Ser. No. 14/907,676, filed on Jan. 26, 2016, which in turn is a National Phase Application of PCT/FR2014/051890 filed on Jul. 22, 2014 and claims priority to French Patent Application No. 13 57666, filed on Aug. 1, 2013, all of which are incorporated by reference.

BACKGROUND

Field of the Invention

The invention relates to a device for diffusing a fragrance such as a scent.

Description of the Related Art

Document FR 2 958 854 discloses a fragrance diffuser comprising:
two pouring plugs mounted top to tail and each having a flow tube,
an insert of porous material fitted between the two pouring plugs,
an external ring provided, facing the insert, with at least one fragrance diffusion opening.

Each pouring plug also comprises a flow hole which allows the fragrance to pass into the porous insert and then to the outside of the device. The fragrance is, for example, contained in a bottle arranged above the diffuser.

Although satisfactory, this diffuser could nevertheless be simplified.

Objects and Summary

To that end, the invention, in a first aspect, is aimed at a fragrance diffusion device, characterized in that it comprises:
two opposing walls spaced apart from one another along a longitudinal axis so as to define between them a cavity which extends transversely as far as a peripheral wall provided with at least one opening for diffusing fragrance to outside the device, said at least one opening placing the cavity in communication with the outside of the device,
at least one wick made of porous material which extends in the cavity along the longitudinal axis passing through the two walls via its two respective opposite ends which each project into an external zone adjacent to the relevant wall,
at least one air intake opening which passes through each wall in such a way as to place each external zone adjacent to each wall in communication with the cavity and therefore with the outside of the device. In the device according to the invention, said at least one wick becomes impregnated with fragrance and thus both diffuses fragrance (situated above the device, notably in an upper bottle) into the cavity and to the outside, via the central portion of said at least one wick which extends into the cavity, and provides drop by drop dripping underneath the device (notably into a lower bottle).

The device according to the invention is therefore simpler than that of the prior art in which the diffusion and dripping functions are separate.

Moreover, in the abovementioned prior art, in order to achieve the drop by drop dripping effect, very small holes (e.g.: 0.2 to 0.5 mm) are needed and these have a tendency to become blocked in the presence of fatty products included in the composition of fragrances (scents). This problem does not arise with the device according to the invention in which the drop by drop dripping function is performed by said at least one porous wick.

Unlike the device of the abovementioned prior art, the intake air that compensates for the volume of fragrance flowing through said at least one wick comes from outside the device. This means that the compensation for air in the bottle that is dispensing its fragrance can be dissociated from the flow of this fragrance and therefore from the drop by drop dripping. In the prior art, the bottles communicate with one another via air-passage and flow tubes. Thus, the pressure or depression in one or other of the bottles has an influence on the drop by drop dripping function (for example when pressure equilibrium needs to be established), something which is not the case with the device according to the invention.

According to other possible features considered in isolation or in combination with one another:
the device comprises, on each side of the two walls, in each external zone adjacent to each wall, fixing means each intended to fix a neck of a bottle to the device;
each wall has a concave overall shape with the concave side facing towards the cavity and comprises a central region;
said at least one opening is situated at the periphery of the central region;
several air intake through-openings are made in each wall, the device comprising shutoff means which, depending on their position, are able to shut off all or some of said openings;
the device comprises a plurality of porous wicks distributed in the cavity;
the device comprises a ball valve system formed in each wall in line with a through-opening in the wall so that the ball of the ball valve system of the upper wall shuts off the corresponding opening and the ball of the ball valve system of the lower wall leaves the corresponding opening uncovered;
the longitudinal axis is a vertical axis of the device.

According to a second aspect, the invention is also aimed at a fragrance diffusion system, characterized in that it comprises:
a diffusion device as briefly described hereinabove,
an upper first bottle having a first neck the opening of which is positioned facing one of the two opposing walls referred to as the upper wall; a lower second bottle having a second neck the opening of which is positioned facing the other wall referred to as the lower wall, the upper first bottle comprising the fragrance which, by impregnating the wick, on the one hand causes the fragrance to diffuse into the cavity and to outside of the device via said at least one opening, and on the other hand causes dripping drop by drop into the lower second bottle.

This system has the same advantages and features as those mentioned in relation to the diffusion device mentioned above and these will therefore not be repeated here.

BRIEF DESCRIPTION OF THE INVENTION

Other features and advantages will become apparent during the course of the following description, given solely by way of nonlimiting example and made with reference to the attached drawings in which.

DETAILED DESCRIPTION

Figure 1:
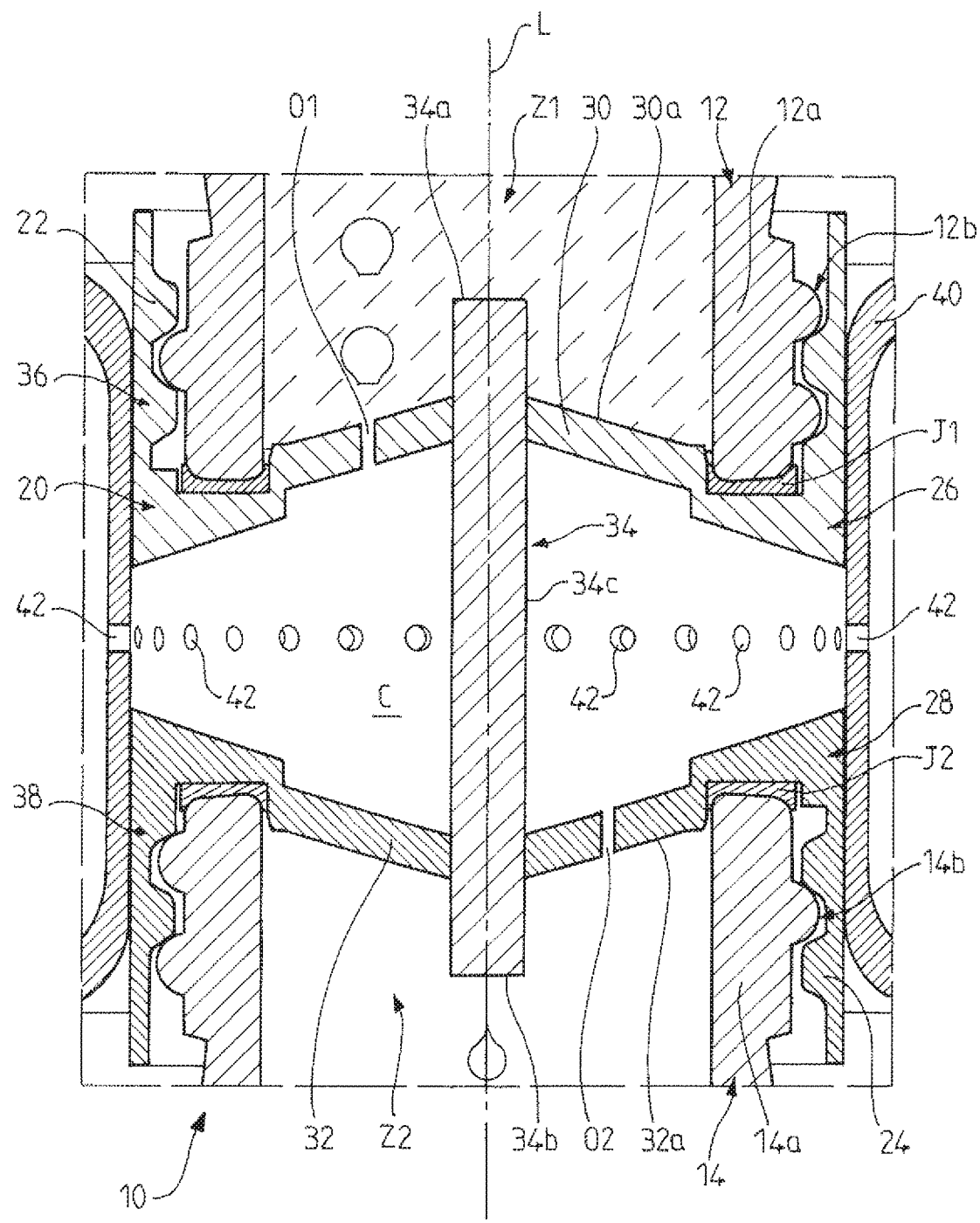
FIG. 1 is a schematic overall view in axial section of a fragrance diffusion device according to a first embodiment of the invention.

As depicted in FIG. 1 and denoted by the general reference 10, a fragrance diffusion system comprises a fragrance diffusion device 20 and two bottles 12, 14, only the respective necks 12a, 14a of which have been depicted.

An upper first bottle 12 containing the fragrance (e.g. an ambient scent) that is to be diffused is mounted on top of the device 20 with its neck 12a oriented downwards.

The device 20 comprises first fixing means 22 which are intended to fix the neck 12a to said device. These fixing means are, for example, produced in the form of an internal screw thread for screwing onto the external screw thread 12b on the external surface of the neck 12a.

A lower second bottle 14 intended to collect undiffused fragrance coming from the upper bottle 12 is mounted under the device 20 with its neck 14a oriented upwards.

The diffusion device 20 comprises second fixing means 24 which are intended to fix the neck 14a to said device. These fixing means are, for example, produced in the form of an internal screw thread for screwing onto the external screw thread 14b on the external surface of the neck 14a. Other fixing means such as snap-fastening means may be envisaged.

The system 10 and its device 20 as well as the two bottles are arranged vertically in FIG. 1 so that the fragrance contained in the upper bottle 12 can flow under gravity.

The device 20 comprises two components, namely an upper component 26 and a lower component 28 positioned facing one another and spaced apart from one another along a longitudinal axis L which in this instance is oriented vertically.

The two components 26, 28 each comprise a wall 30, 32 arranged one facing the other and which between them define a central cavity C. The walls 30, 32 are perforated in their middle (central region) so as to allow a porous wick 34 to extend axially in the cavity C between the walls, being held in these walls via two respective opposite ends 34a, 34b. These two opposite ends 34a, 34b pass through the respective walls 30, 32 and each project into a zone external to the device (Z1, Z2) and adjacent to the relevant wall.

As depicted in FIG. 1, each external zone is a zone internal to the neck of a bottle.

The wick is made of porous material of known type.

The walls 30, 32 extend transversely from their central region towards their periphery where a wall 36, 38 extends axially. The two axially extending walls 36, 38 of the components 26, 28 extend in opposite directions and away from the cavity C. The fixing means 22, 24 are formed on the interior surface of these walls. It will be noted that the neck 12a, 14a of each bottle, once fixed to the device 20, presses against a respective seal J1, J2 formed in a recess of the external face 30a, 32a of the relevant transversely extending wall.

As depicted, each transverse wall 30, 32 has a concave overall shape with the concave side facing towards the cavity C. Each wall is more particularly in the shape of a funnel converging towards the central region.

Each component 26, 28 generally has axial symmetry of revolution, give or take a few embodiment details. Thus, the axially extending walls 36, 38 each have a substantially cylindrical shape, making them skirt like.

The device 20 also comprises at its periphery a peripheral wall 40 having a ring like overall shape surrounding the assembly formed of the two opposing components 26, 28 and of the separating central cavity C. This peripheral wall 40 forms a trim element and is fixed to each of the aforementioned assemblies for example by bonding, welding or some other suitable means.

The peripheral wall 40 is provided with at least one opening 42 for diffusing fragrance to outside the device. Said at least one opening 42 is made in that region of the wall that is situated around the cavity C so as to place this cavity in communication with the outside of the device. In practice, for better distribution of the diffusion of fragrance, several openings 42 are arranged around the periphery of the peripheral wall 40 as depicted in FIG. 1, in an equatorial region of the device.

Each of the transversely extending walls 30, 32 comprises at least one air intake opening O1, O2 which passes through the thickness thereof so as to place each external zone Z1, Z2 adjacent to each wall in communication with the central cavity C and therefore with the outside of the device via the openings 42.

In the configuration of FIG. 1, said at least one air intake opening is situated at the periphery of the central region of each wall, in a manner that is offset from the central position of the wick 34.

It will be noted that several openings may be provided in each wall 30, 32 so as to increase the flow rate and therefore the speed of drop by drop dripping. Specifically, this speed is notably dependent on the ability of the device to take air in.

When the fragrance diffusion system 10 is in operation, the liquid (fragrance) present in the inverted upper bottle 12 impregnates the upper end 34a of the wick 34 and flows inside same over the entire length thereof. Because the wick is impregnated with liquid, it diffuses the fragrance radially or transversely from its central part 34c which is in contact with the air inside the cavity C. The cavity C is a diffusion zone through which the fragrance diffuses as far as the openings 42, through which it passes in order to leave the device 20.

The wick 34 creates something of a suction on the liquid in the bottle 12 and therefore creates a depression in said bottle (pumping effect). This depression is compensated for by the external air that enters the bottle via said at least one air intake opening O1.

Not all of the liquid with which the wick is impregnated diffuses into the cavity. Specifically, a proportion of the liquid flows along the wick as far as the open lower end 34b thereof and flows into the lower bottle 14, in the form of drop by drop dripping. When the "non-diffused" liquid has passed into the lower bottle the diffusion phenomenon ceases. The capacity of the lower bottle is dimensioned so that the level of the liquid transferred into the bottle is situated below the lower end 34b of the wick.

When there is no longer any liquid in the upper bottle 12 and the lower bottle 14 is (at least partially) full, the system is inverted: the lower bottle 14 becomes the upper bottle and vice versa, and the mode of operation described hereinabove is repeated.

Figure 3:
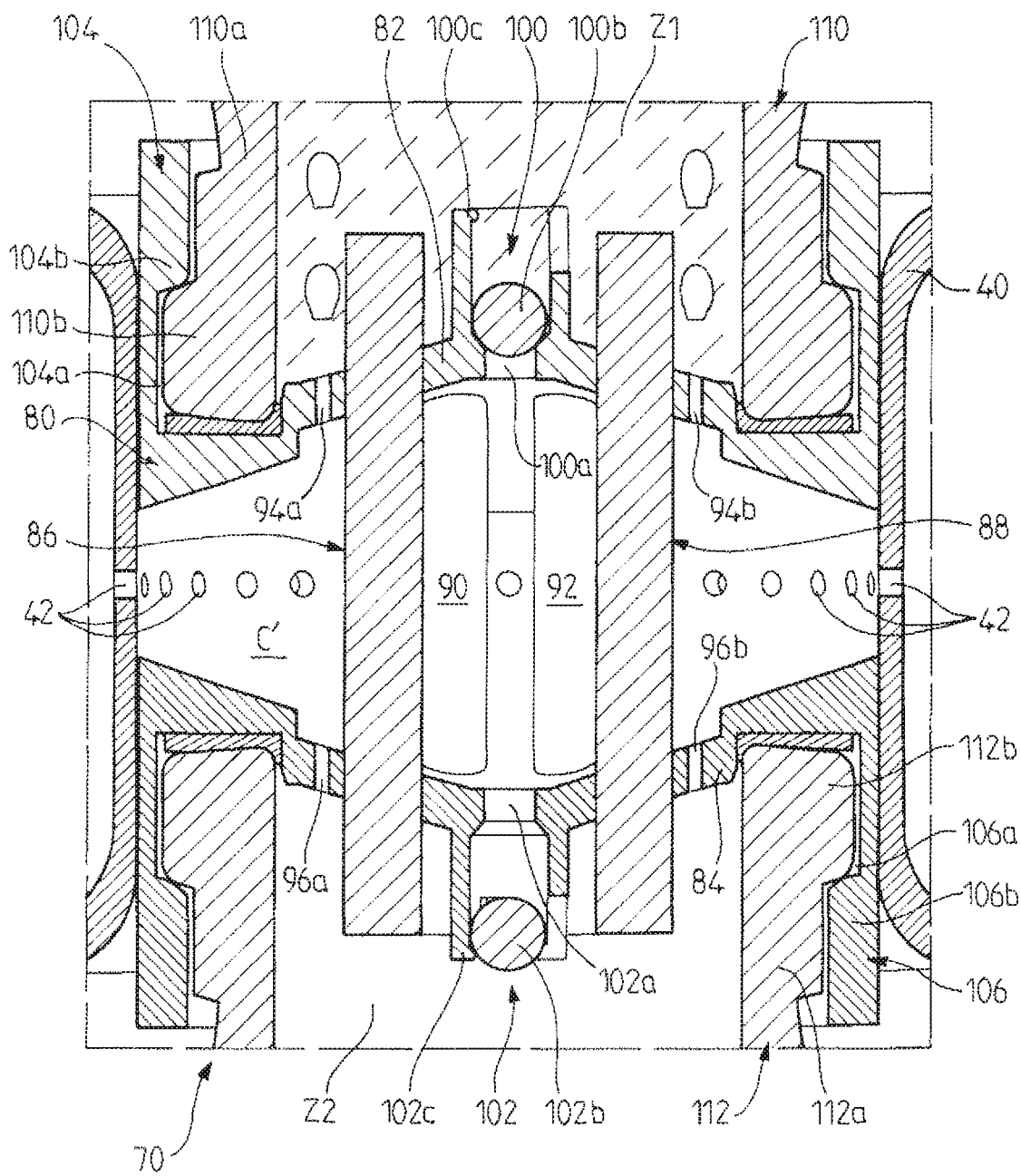
FIG. 3 is a schematic overall view in axial section of a fragrance diffusion device according to a second embodiment of the invention.

It will be noted that the flow rate of the liquid in the wick and therefore the speed of the drop by drop dripping flow is dependent on the diameter of the air intake opening or openings O1, O2. This speed may also be dependent on the length, density and diameter of the wick, or even on the number of wicks, when there are several of these (FIG. 3).

The walls 30 and 32 have been rendered hollow or concave in their central region surrounding the wick so that the opening or openings O2 present in the wall 32 (and the same applies to the opening or openings O1 present in the wall 30 when the system is inverted) are arranged at a level above a low point of the wall surrounding the wick and around which the liquid originating from potential seepage could accumulate. Such an arrangement considerably reduces the risk of seepage liquid obstructing the opening or openings O2 while the system is in operation.

Figure 2:
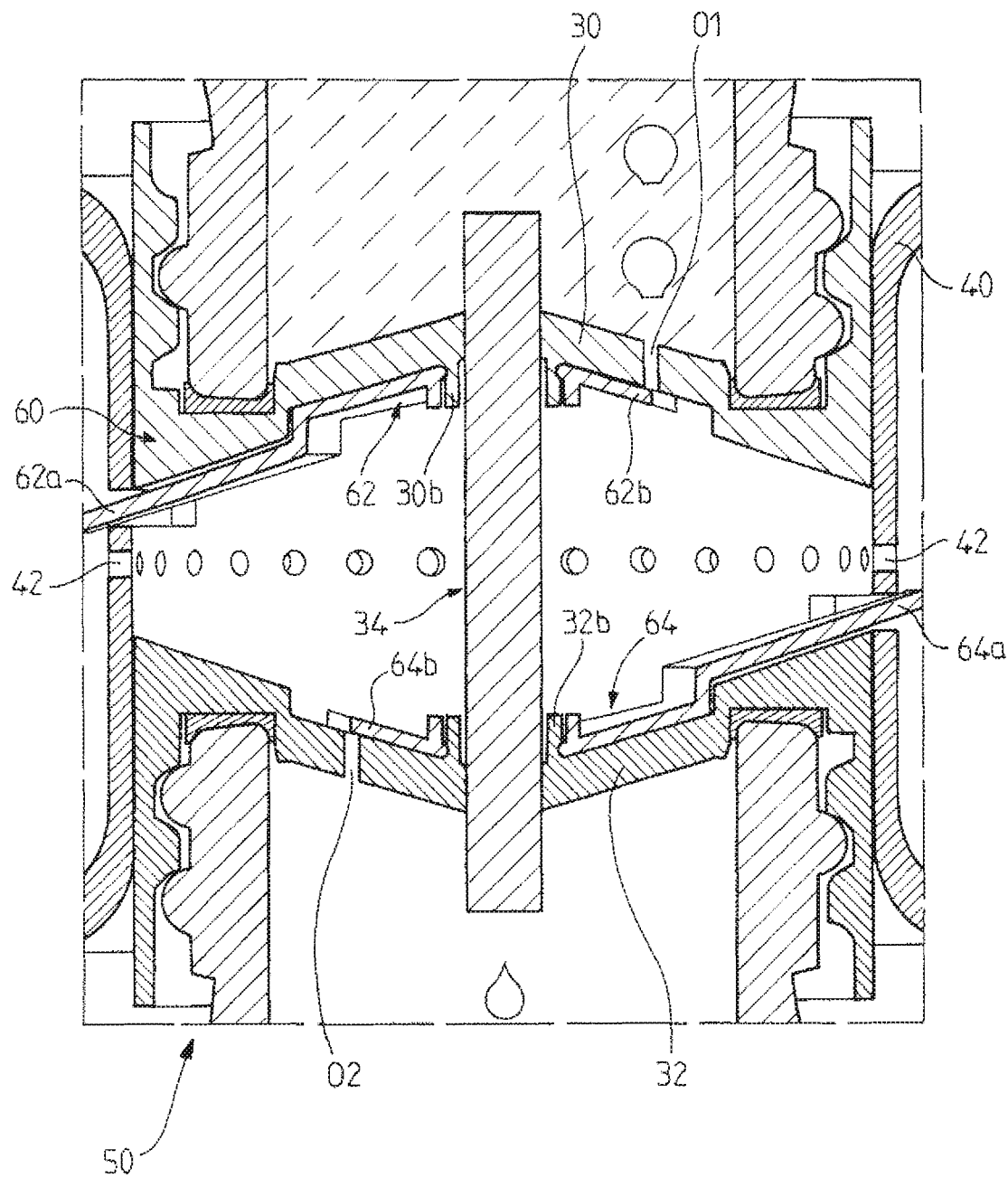
FIG. 2 illustrates an alternative form of embodiment of the device of FIG. 1.

FIG. 2 illustrates an alternative form of embodiment of the system of FIG. 1. The system 50 according to this alternative form comprises a diffusion device 60 which comprises means for regulating the ingress of air through said at least one air intake opening O1 (or O2). The other elements of the system and of the device are unchanged with respect to FIG. 1 and therefore keep the same references.

The regulating means of the device 60 allow the flow rate of liquid through the wick and therefore the speed at which the drops are formed to vary.

In the example illustrated in FIG. 2 (this figure is almost a mirror-image of FIG. 1), each wall comprises several air intake openings (O1 for the wall 30 and O2 for the wall 32), only one of which has been depicted. More specifically, the device comprises regulating means associated with each series of openings O1 and O2 of each plate 30, 32.

For example, these means each adopt the form of a shutoff member 62, 64 which is mounted with the ability to rotate about a central hub (extension 30b, 32b) secured to the associated wall 30, 32 (the wick 34 is mounted inside these hubs) and which can be actuated by a control knob 62a, 64a (regulating knob) arranged on the outside of the device. Additional openings, which are enlarged in comparison with the openings 42, have been made in the peripheral wall 40 to allow the passage of the associated control knob. The shutoff member comprises a shutoff end 62b, 64b which, by rotation controlled by the knob, shuts off one or more air intake openings or, on the other hand, uncovers them. The shutoff member may thus have a shutoff end shape suited to best shutting off the opening or openings. The member may for example adopt the form of an eccentric cam.

A diffusion system 70 according to a second embodiment is depicted in FIG. 3 and comprises a diffusion device 80.

The device 80 still comprises two transversely extending walls 82, 84 facing one another and between them defining a central diffusion cavity C' or zone.

Several porous wicks are arranged in the cavity C' and are mounted via their two opposite through-ends in the two respective walls 82, 84.

Four wicks may, for example, be counted, of which two, 86, 88, are depicted in the foreground and two, 90, 92, in the background.

These wicks are evenly distributed about the central region of each wall 82, 84 which is hollowed or concave (generally funnel-shaped wall end). A different number and layout of wicks may be envisioned.

Several air intake openings 94a, 94b and 96a, 96b are provided in each wall 82, 84. Two openings are depicted for each wall. However, a different number and layout of openings may be envisioned.

In the example of FIG. 3, the openings are distributed at the external periphery of the wicks. The central region of each wall 82, 84 incorporates a ball valve system 100, 102 aligned with a through-opening in the relevant wall and opening into the cavity C.

The ball valve system 100 (or 102) comprises a through-opening 100a (or 102a) the upper edges of which form a valve seat, and a ball 100b (or 102b) mounted inside a well 100c (or 102c) extending axially from the edges of the opening in the zone Z1 (or Z2). Under the effect of gravity, the ball 100b rests on its valve seat.

The ball 100b that forms a valve shuts off the opening 100a to prevent liquid present in the neck of the upper bottle from passing directly through this opening.

The ball 102b, on the other hand, rests under the effect of gravity on a shoulder formed on the internal edge of the free end of the well 102c, without, however, shutting off the well.

When liquid seeps into the cavity, it flows as far as the opening 102a and into the well 102c, then into the lower bottle.

It will be noted that the axially extending walls 104 and 106 of the device have fixing means that differ from the fixing means 22 and 24 of FIG. 1.

Specifically, the fixing means comprise, configured in the wall 104 (or 106) and on the inside thereof, at least one cavity 104a (or 106a) placed to the rear of at least one thicker wall portion 104b (or 106b). This cavity is able to accommodate an external stud 110b formed on the neck 110a of the upper bottle 110 and thus able to hold the neck of the bottle in this immobilized position with respect to the device 80.

It will be noted that these fixing means of the device comprise several cavities and thickened portions at the circumference of the wall 104 (or 106). The neck 110a (or 112a) is provided with several external studs locally distributed at the periphery of the neck. Through a movement of axial insertion of the neck 110a (or 112a) into the axial component 104 (or 106) and of rotation, the studs become housed in the corresponding cavities to axially immobilize the corresponding bottle.

According to an alternative form that has not been depicted, the neck 110a (or 112a) does not have external studs but has a continuous shoulder around its entire external periphery. The neck is forcibly inserted into the fixing end piece 104, 106 which is made of a deformable material (e.g. of plastic).

All the other features described in relation to FIG. 1 are found again here, perform the same functions and afford the same advantages.

The invention claimed is:

1. A Fragrance diffusion system, comprising a diffusion device which comprises:
   two opposing walls spaced apart from one another along a longitudinal axis so as to define between them a cavity which extends transversely as far as a peripheral wall provided with at least one opening for diffusing fragrance to outside the device, said at least one opening placing the cavity in communication with the outside of the device,
   at least one wick made of porous material which extends in the cavity along the longitudinal axis passing through the two walls via its two respective opposite ends which each project into an external zone adjacent to the relevant wall,
   at least one air intake opening which passes through each wall of said two opposing walls in such a way as to place each external zone adjacent to each wall of said two opposing walls in communication with the cavity and therefore with the outside of the device, an upper first bottle having a first neck the opening of which is positioned facing one of the two opposing walls referred to as the upper wall, a lower second bottle having a second neck the opening of which is positioned facing the other wall referred to as the lower wall, the upper first bottle comprising the fragrance which, by impregnating the wick, on the one hand causes the fragrance to diffuse into the cavity and to outside of the device via said at least one opening, and on the other hand causes dripping drop by drop into the lower second bottle, the lower second bottle having a capacity which is dimensioned so that the level of the liquid transferred into said lower second bottle is situated below a lower end of the wick.

2. Fragrance diffusion system according to claim 1, wherein said system comprises, on each side of the two walls, in each external zone adjacent to each wall, fixing means each intended to fix a neck of either one of the upper first bottle and lower second bottle to the device.

3. Fragrance diffusion system according to claim 1, wherein each wall has a concave overall shape with the concave side facing towards the cavity and comprises a central region.

4. Fragrance diffusion system according to claim 1, wherein said at least one opening is situated at the periphery of the central region.

5. Fragrance diffusion system according to claim 1, wherein several air intake through-openings are made in each wall, the device comprising shutoff means which, depending on their position, are able to shut off all or some of said openings.

6. Fragrance diffusion system according to claim 1, wherein said system comprises a plurality of porous wicks distributed in the cavity.

7. Fragrance diffusion system according to claim 1, wherein said system comprises a ball valve system formed in each wall in line with a through-opening in the wall so that the ball of the ball valve system of the upper wall shuts off the corresponding opening and the ball of the ball valve system of the lower wall leaves the corresponding opening uncovered.

8. Fragrance diffusion system according to claim 1, wherein the longitudinal axis is a vertical axis of the device.

9. Fragrance diffusion system according to claim 1, wherein the two opposing walls extend transversely from their central region towards their periphery.

10. Fragrance diffusion system according to claim 1, wherein the speed of the drop by drop dripping flow is dependent on the diameter of the at least one air intake opening.

11. Fragrance diffusion system according to claim 1, wherein the speed of the drop by drop dripping flow is dependent on at least one of the following: the length of the wick, the density of the wick, the diameter of the wick, the number of wicks when there are several.

12. Fragrance diffusion system according to claim 1, wherein said peripheral wall has a ring like overall shape surrounding the assembly formed of the two opposing walls and of the separating central cavity.

13. Fragrance diffusion system according to claim 1, wherein the peripheral wall is a unitary wall structure peripherally enclosing said cavity.

14. Fragrance diffusion system according to claim 1, wherein each air intake opening among of said at least one air intake openings is spaced apart from the opening allowing the passage of the wick.

\* \* \* \* \*